United States Patent [19]

Dumoulin

[11] 3,975,294

[45] Aug. 17, 1976

[54] SURFACE ACTIVE COMPOSITION

[75] Inventor: Jean Dumoulin, Villeurbame, France

[73] Assignee: Rhone-Poulenc S.A., Paris, France

[22] Filed: Nov. 2, 1973

[21] Appl. No.: 412,141

[30] Foreign Application Priority Data

Nov. 3, 1972 France............................ 72.38957

[52] U.S. Cl.................................... 252/354; 106/2; 106/287 SB; 252/117; 252/118; 252/312; 252/316; 260/29.2 M; 424/59; 424/63; 424/184; 428/409; 428/447

[51] Int. Cl.².................. B01F 17/10; B01F 17/42; C11D 9/32; C08L 43/04

[58] Field of Search............ 252/309, 312, 354, 8.7, 252/8.75, 117, 121, 118

[56] References Cited

UNITED STATES PATENTS

| | | | |
|---|---|---|---|
| 3,338,830 | 8/1967 | Stokes et al. | 252/8.7 X |
| 3,428,560 | 2/1969 | Olsen | 252/8.7 |
| 3,508,611 | 4/1970 | Davis et al. | 252/309 X |
| 3,663,445 | 5/1972 | Augustin et al. | 252/117 |

*Primary Examiner*—Herbert B. Guynn
*Attorney, Agent, or Firm*—Cushman, Darby & Cushman

[57] ABSTRACT

A surface active composition comprises by weight:
a. 45 to 90% of at least one n-alkyl monoether of a polyethylene glycol, containing 4 to 9 —CH$_2$CH$_2$O— units, the n-alkyl radicals containing 5 to 15 carbon atoms,
b. 5 to 35% of a sodium dialkylsulphosuccinate, the linear or branched alkyl radicals containing 6 to 12 carbon atoms,
c. 2 to 17% of at least one acid selected from oleic, linoleic, linolenic and ricinoleic acid and
d. 1.5 to 12% of at least one amine selected from triethanolamine and N-hydroxyethylmorpholine.

The composition may be used as an emulsifier with diorganopolysiloxanes to form transparent micro-emulsions or transparent gels or to introduce silane cross-linking agents into catalyzed aqueous polysiloxane emulsions to cross-link the emulsion.

4 Claims, No Drawings

SURFACE ACTIVE COMPOSITION

The present invention relates to a surface-active composition which can be used either for the preparation of transparent aqueous micro-emulsions or transparent gels containing organo-silicon compounds or for facilitating or permitting the introduction of organo-silicon compounds into conventional aqueous emulsions containing organic polymers and/or organo-silicon polymers.

These organo-silicon compounds can be monomers or polymers and may or may not possess hydrolysable groups.

It is known that aqueous emulsions of organo-polysiloxane polymers can be used for various applications such as the waterproofing of textiles, the non-stick treatment of paper, the impregnation of masonry, mould release applications in general, and the manufacture of cosmetic products and antifoaming products. These emulsions are obtained by passing mixtures containing principally one or more organopolysiloxane polymers, water and conventional surface-active agents through a colloid mill turning at several thousand revolutions per minute.

These emulsions are currently very widely used (Chemistry and Technology of Silicones, W. Noll (1968) pages 428 to 431), but they suffer from various disadvantages; their stability is sometimes precarious and this situation is difficult to remedy, and furthermore their milky and opaque appearance is less pleasant and attractive, especially for the presentation of cosmetic products, than that of limpid solutions or transparent gels.

Further, it is known that in order to introduce organosilicon compounds, whether monomers or polymers, into aqueous emulsions which contain organic polymers or organo-silicon polymers it is necessary first to convert the former compounds into aqueous emulsions; they are then incorporated in this form. A small number of the compounds, which possess strongly hydrophilic groups, can optionally be added as they are, at the risk of breaking the emulsions, but in the majority of cases the insolubility of the compounds prevents their being introduced in this way. This aqueous emulsification requires a suitable apparatus and the use of rather large quantities of water; furthermore, it does not allow organo-silicon compounds with hydrolysable groups, for example of the alkoxy or polyalkoxy type, to be used, which correspondingly restricts the range of choice of compounds and range of applications.

The present invention provides a surface-active composition comprising, by weight:
a. 45 to 90% of at least one n-alkyl monoether of a polyethylene glycol, containing 4 to 9 —$CH_2CH_2O$— units, the n-alkyl radicals containing 5 to 15 carbon atoms,
b. 5 to 35% of a sodium dialkylsulphosuccinate, the linear or branched alkyl radicals containing 6 to 12 carbon atoms,
c. 2 to 17% of at least one acid selected from oleic, linoleic, linolenic and ricinoleic acid and
d. 1.5 to 12% of at least one amine selected from triethanolamine and N-hydroxyethylmorpholine.

The n-alkyl monoethers of polyethylene glycols are polymers which have been commercially available for many years. They are primarily employed as surface-active agents. Their method of manufacture most frequently gives mixtures of polymers of which the molecular weights are more or less close to one another; however, in order to be usable as constituents of the mixtures according to the invention, these polymers or their mixtures must contain an average number of —$CH_2CH_2O$— units, and their terminal n-alkyl group must contain a number of carbon atoms, which fall within the ranges mentioned above.

The sodium dialkylsulphosuccinates form part of an already long-established and very readily obtainable series of products generally used as anionic emulsifiers; however, the commercially available products are not always pure and can contain alkanols which are by-products from their manufacture.

By way of illustration, it is possible to use sodium di(2-ethylhexyl)sulphosuccinate, sometimes mixed with ethanol and water, sodium dihexylsulphosuccinate, sodium dinonylsulphosuccinate and sodium dioctylsulphosuccinate.

The compositions according to the present invention can be prepared by simple stirring of the various constituents introduced in any sequence and in the above-mentioned proportions; however, it is preferable to add the aliphatic acid and the amine last so as to facilitate the solubilisation of the salt formed.

The production, by means of the mixtures according to the invention, hereafter called mixtures E, of transparent aqueous micro-emulsions or transparent gels is also easy and does not require special operations. However, it is advisable to prepare beforehand a homogeneous mixture consisting of the mixture E and of the desired organo-silicon compounds; this mixture, which will hereafter be referred to as mixture T, can contain 0.1 to 15 parts by weight of mixture E, preferably 0.3 to 12 parts, per 1 part of organo-silicon compounds.

This mixture T is then introduced into a suitable container containing the water and the other ingredients, or is even introduced before the addition of these latter components. Simple stirring suffices to solubilise the whole mixture. In addition to water and the mixture T, the ingredients added can contain soluble organic derivatives such as perfume, dyestuffs, alcohols, polyols, aminoalcohols, ketones, salts of organic acids and soluble inorganic derivatives such as acids, bases and their salts; furthermore, to manufacture transparent gels, it is possible to employ thickening agents which are water-soluble or swell in water, such as regenerated or non-regenerated substituted celluloses, polyvinyl alcohols and carboxyvinyl polymers of high molecular weight.

The amount of mixture T which is added represents at most 60% of the weight of the micro-emulsions or gels, preferably 55%, and depends principally on the nature and proportion of the organo-silicon compounds to be solubilised and on the envisaged application. The total amount of the organo-silicon compounds added can furthermore vary very greatly and more precisely represents 0.05 to 15% of the weight of the transparent compositions or transparent gels, preferably 0.1 to 13%.

Certain of the organo-silicon compounds which are difficult to solubilise can more easily be converted into micro-emulsions by addition of alkanols with 4 to 15 carbon atoms. Thus, if the addition of a certain amount of the mixture T to an aqueous solution causes cloudiness, it suffices then to add a small quantity of an alkanol, such as butanol, 2-ethylhexanol, octanol or dodecanol, in order to cause the cloudiness to disappear; at this stage mixture T can again be added until cloudiness appears, and alkanol can then again be introduced, and this procedure can be continued until the desired concentration of organo-silicon compounds is obtained.

In general, the proportion of alcohol added does not exceed 30% by weight of the mixture E.

As regards the introduction of organo-silicon compounds into aqueous emulsions, which is another embodiment of the present invention, simple addition of the mixture T to such emulsions can be used; however, slight stirring facilitates the dispersion of the whole. For this application the mixture T can contain, in addition to the mixture E and the organo-silicon compounds which are distributed in accordance with the proportions already indicated, products which are insoluble or sparingly soluble in water, with the proviso that they do not interfere with either the stability or the homogeneity of the mixture T resulting therefrom. Amongst these products there may be mentioned organo-metallic salts and oxides and liquid organic polymers.

The proportion of the mixture T incorporated is at most 25% by weight of the emulsions modified in this way and preferably 20%, and also depends on the structure of the organo-silicon compounds and on their desired applications. The amount of organo-silicon compounds introduced represents 0.02 to 13% of the weight of the modified aqueous emulsions, preferably 0.1 to 12%.

The organo-silicon compounds which can be incorporated either into the micro-emulsions or into the aqueous emulsions can be polymers or monomers which may or may not contain hydrolysable groups.

The following may be mentioned by way of illustration: organopolysiloxane polymers possessing 0.8 to 2.6 organic groups per silicon atom and formed of units chosen from the group consisting of those of the formulae $R_3SiO_{0.5}$, $R_2SiO$, $RSiO_{1.5}$, $SiO_2$ and $$O_{\frac{3-b}{2}}R_bSiQ_nSiR_bO_{\frac{3-b}{2}}$$

in which the symbol R represents a monovalent organic group possessing 1 to 20 carbon atoms amongst other atoms, the symbol Q represents a divalent hydrocarbon radical having 1 to 12 carbon atoms, the symbol $a$ represents zero or 1 and the symbol $b$ represents zero, 1 or 2. More precisely, the symbol R can be directly linked to a silicon atom by an Si—C, Si—O—C or Si—N—C bond and the symbol Q can be alkylene radical having 1 to 8 carbon atoms or an arylene radical having 6 to 12 carbon atoms.

These copolymers, which can be linear, cyclic or branched and can optionally contain up to 15% of their weight of hydroxyl groups linked to silicon atoms are in the form of liquid, oily or resinous substances, the latter most frequently being dissolved in the customary organic solvents.

Also to be mentioned by way of illustration are the monomers of formulae $R_4Si$ and $R_3SiQ_aSiR_3$, in which the symbols R, Q and $a$ have the abovementioned meaning.

More specifically, these monomers can be chosen from amongst the methyl(and/or phenyl)alkoxysilanes and disilanes, methyl(and/or phenyl)polyalkoxysilanes, bis[methyl(and/or phenyl) alkoxysilyl]alkanes, bis[methyl(and/or phenyl)alkoxysilyl] benzenes, alkoxysilanes and polyalkoxysilanes.

The aqueous micro-emulsions can be used in numerous fields of application such as the care of glassware, window-panes, ceramics and household interiors, skin care (sun lotion, pre-shave lotion and after-shave lotion) and the manufacture of beauty products.

The transparent gels are more particularly of value as cosmetic products because of their ease of application.

The introduction of the most diverse organo-silicon compounds, allowed by the use of the mixture E of the invention, into aqueous emulsions enlarge the field of use of these compounds. Thus, organosilanes or polysiloxanes which are usually unstable in an aqueous medium can now be employed for modifying, for example, natural or synthetic rubber latices or emulsions of organic or organo-silicon resins, or for cross linking organo-silicon polymers dispersed in aqueous emulsions.

In particular, in this latter case, the use of such combinations makes it possible easily to deposit thin continuous films of protective and non-stick organopolysiloxane materials on the most diverse substrates such as timber, paper, leather, cardboard, masonry, plastics, brickwork, plaster, metals and horn.

The examples which follow illustrate the invention. (Throughout the text which follows, the parts are expressed by weight).

EXAMPLE 1

A. A composition containing the following is used:

| | |
|---|---|
| distilled water | 982 parts |
| hexylene glycol | 5 parts |
| ammonia, 22° Baumé strength | 2 parts |
| 1% strength solution of Brilliant Green in water. | 1 part |
| organopolysiloxane polymer of viscosity 28.5 cPo at 25° C, consisting of units of formulae $(CH_3)_3SiO_{0.5}$ and $C_6H_5SiO_{1.5}$, present in the respective numerical ratio of 1.6/1 | 2 parts |
| emulsifier $E_1$ | 8 parts |

The emulsion $E_1$ is itself formed of the following, the amounts being by weight:

70% of the n-undecyl monoether of a polyethylene glycol possessing an average of 6—-$CH_2CH_2O$— units 15% of sodium di(2-ethylhexyl)sulphosuccinate 9% of oleic acid 6% of triethanolamine To prepare this composition, the water and the mixture consisting of the emulsion $E_1$ and the organopolysiloxane polymer are poured into a suitable vessel, the whole is gently stirred and the remainder of the compounds is then added in any desired sequence. This composition is a light-green limpid liquid which is stable on storage.

It is applied to dirty window-panes by means of a cloth and after wiping with a dry and clean cloth it is found that the windows have become clear and bright. It is furthermore found that the clean appearance of the window-panes persists for some time because of the fact that the dust suspended in the air adheres poorly to the surface of these windows. Hence, simple periodic wiping suffices to restore their lustre completely.

B. 5 parts of the mixture formed from 8 parts of the emulsifier $E_1$ and 2 parts of the organopolysiloxane polymer of viscosity 28.5 cPo at 25° C are taken and introduced into 5 parts of water with simple manual stirring. A limpid solution which is stable on storage and which contains 10% by weight of organopolysiloxane polymers is obtained.

This solution is diluted 10-fold with water and the new limpid solution thus formed is applied by means of a cloth to varnished mahogany furniture which is dusty and shows finger marks. After wiping, the furniture is clean and glossy and - as in the case of the windows cleaned with the aid of the solution referred to under A, merely simple wiping from time to time suffices to restore the lustre of this furniture.

EXAMPLE 2

A composition containing the following is used:

| | |
|---|---|
| distilled water | 980 parts |
| ammonium acetate | 10 parts |
| diorganopolysiloxane oil of viscosity 200 cPo at 25° C, of average formula | 3 parts |

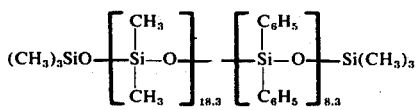

| | |
|---|---|
| emulsifier $E_2$ | 7 parts |

Emulsifier $E_2$ itself consists of the following, the amounts being by weight:
- 50% of the n-octyl monoether of a polyethylene glycol possessing on average 7—$CH_2CH_2O$— units
- 25% of sodium di(hexyl)sulphosuccinate
- 15% of linoleic acid
- 10% of triethanolamine.

To prepare this composition, the water and the mixture of diorganopolysiloxane oil and emulsion $E_2$ are introduced into a vessel in that order, the whole is stirred and the other constituents are added in any desired sequence. The composition is a limpid liquid which is stable on storage.

Glassware is cleaned with a cloth impregnated with this liquid and after wiping with a dry cloth a remarkable brightness results, which shows marked non-stick properties towards dust and stains.

EXAMPLE 3

A composition containing the following is used:

| | |
|---|---|
| distilled water | 59.15 parts |
| dihydroxyacetone | 4 parts |
| d-panthenol | 0.2 part |
| polyethylene glycol of molecular weight 400 | 1.4 parts |
| caramel brown dyestuff | 0.05 part |
| scent | 0.4 part |
| diorganopolysiloxane oil of viscosity 88 cPo at 25° C, possessing —$(CH_2)_3OC\!-\!C_6H_4\!-\!N(CH_3)_2$ groups, described in Example 4 of French Patent 1,527,781 | 3.2 parts |
| emulsifier $E_3$ | 31.6 parts |

The emulsifier $E_3$ is itself formed of the following, the amounts being by weight:
- 85% of the n-tetradecyl monoether of a polyethylene glycol containing an average of 5.5—$CH_2CH_2O$— units
- 7% of sodium dioctylsulphosuccinate as a 75% strength solution by weight in a mixture of water and ethanol in the weight ratio of 66/33
- 5% of oleic acid and
- 3% of triethanolamine.

To prepare this composition, the water and all the ingredients except for the diorganopolysiloxane oil and the emulsifier $E_3$ are introduced into a vessel; after a homogeneous solution has been obtained, the mixture of the last two components is added. This composition is a limpid liquid which is stable on storage.

It is used as a sun lotion (the

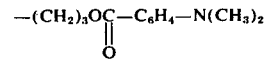

groups linked to the silicon atoms of the diorganopolysiloxane oil play the role of a filter for ultraviolet light in the region responsible for erythema) and it is found that it is very effective in protecting the skin against the rigours of the sun whilst ensuring rapid and even tanning.

EXAMPLE 4

A composition containing the following is used:

| | |
|---|---|
| distilled water | 156 parts |
| polyethylene glycol of molecular weight 600 | 6 parts |
| triethanolamine | 4 parts |
| santaline | 1 part |
| polyoxyethyleneated sorbitan monolaurate | 20 parts |
| acid thickener based on a carboxyvinyl polymer of high molecular weight | 3 parts |
| diorganopolysiloxane oil of viscosity 88 cPo at 25° C, as previously used in Example 3 | 3 parts |
| emulsifier $E_1$ as used in Example 1 | 7 parts |

To prepare this composition, the acid thickener is intimately mixed beforehand with polyethylene glycol, whilst the diorganopolysiloxane oil is intimately mixed beforehand with the emulsifier $E_1$. This latter mixture is then introduced into a suitable vessel containing the water, the triethanolamine, the santaline and polyoxyethyleneated sorbitan monolaurate.

After a limpid solution has been obtained, the mixture of acid thickener and polyethylene glycol is dispersed therein. The composition has the appearance of a transparent gel which is stable on storage. It is used as a sun cream and it is found that it protects the skin and that it is easy to apply.

EXAMPLE 5

A solution containing the following is used:

| | |
|---|---|
| distilled water | 83 parts |
| boric acid | 0.1 part |
| propylene glycol | 1 part |
| menthol | 0.1 part |
| sodium methyl para-hydroxybenzoate | 0.1 part |
| ethyl para-hydroxybenzoate | 0.03 part |
| allantoin | 0.17 part |
| methyloctylpolysiloxane oil of viscosity 575 cPo, at 25° C, blocked by trimethylsiloxy units | 0.4 part |

-continued

| | |
|---|---|
| emulsifier E₄ | 1.6 parts |

The emulsifier E₄ is itself formed of the following, the amounts being by weight:

- 70% of a mixture of n-alkyl monoethers of polyethylene glycols possessing on average 5—$CH_2CH_2O$— units each and obtained by the reaction of a mixture of linear alkanols containing 6 to 14 carbon atoms with ethylene oxide
- 19% of sodium (2-ethylhexyl)sulphosuccinate
- 9% of oleic acid
- 2% of triethanolamine.

To prepare this composition, the water followed by the mixture of methyloctylpolysiloxane oil and emulsifier E₄ are introduced into a suitable vessel. Simple stirring gives a homogeneous solution to which the other ingredients are added in any desired sequence.

This composition has the appearance of a limpid liquid which is still stable after 6 months' storage in glass bottles. It is used as an after-shave lotion by simple application to the skin and it is found that the presence of the silicone oil rapidly eliminates the burning sensation caused by the razor and makes the skin soft.

EXAMPLE 6

A composition containing the following is used:

| | | |
|---|---|---|
| distilled water | 87.45 | parts |
| allantoin | 0.15 | part |
| sodium methyl para-hydroxybenzoate | 0.1 | part |
| menthol | 0.1 | part |
| scent | 0.5 | part |
| ethyl alcohol | 8 | parts |
| 1% strength solution of Brilliant Green in water | 1 | part |
| organic monoether of a polyethylene glycol possessing an average of 33-$CH_2CH_2O$— units, obtained from castor oil and ethylene oxide | 0.5 | part |
| organic monoether of a polyethylene glycol possessing an average of 8-$CH_2CH_2O$— units, obtained from beta-naphthol and ethylene oxide | 0.2 | part |
| methylpropylpolysiloxane oil of viscosity 300 cPo at 25° C, blocked at each chain end by a trimethylsiloxy unit | 0.4 | part |
| emulsifier E₅ | 1.6 | parts |

The emulsifier E₅ is itself formed of the following by weight:

- 58% of the n-heptyl monoether of a polyethylene glycol possessing an average of 4—$CH_2CH_2O$— units
- 33% of sodium dinonylsulphosuccinate
- 3% of linolenic acid
- 6% of triethanolamine.

To prepare this composition, the water and the mixture of the methylpropylpolysiloxane oil and the emulsifier E₅ are introduced into a vessel. After a limpid solution has been obtained, the other ingredients are added in any desired sequence. The composition is homogeneous and stable on storage. It is used as an after-shave lotion and it is found that it easily eliminates the burning sensation caused by the razor and makes the skin soft and smooth.

EXAMPLE 7

An aqueous emulsion (G) containing the following is used:

| | |
|---|---|
| α-ω-dihydroxydimethylpolysiloxane oil of viscosity 14,500 cPo at 25° C | 6 parts |
| n-decyl monoether of a polyethylene glycol possessing an average of 4-$CH_2CH_2O$— units | 0.24 part |
| n-decyl monoether of a polyethylene glycol possessing an average of 6-$CH_2CH_2O$— units | 0.2 part |
| n-tridecyl monoether of a polyethylene glycol possessing an average of 20-$CH_2CH_2O$— units | 0.06 part |
| water | 93.5 parts |

For the catalysis of this emulsion, 0.6 part of an emulsion (H) consisting of the following is used:

| | |
|---|---|
| dibutyl-tin dilaurate | 3.3 parts |
| methylcyclohexane | 1.5 part |
| polyvinyl alcohol of saponification number 105, of which the viscosity of a 4% strength aqueous solution is about 25 cPo at 25° C | 0.2 part |
| water | 5 parts |

For cross-linking the first emulsion, 0.6 part of a solution (M) consisting of the following is used:

| | |
|---|---|
| vinyltris(methoxyethoxy)silane | 8 parts |
| emulsifier E₁ used in Example 1 | 2 parts |

The 3 compositions (G), (H) and (M) are mixed and simple stirring gives an aqueous emulsion which is stable for at least 72 hours at ambient temperature. This emulsion is deposited at the rate of 20 g/m² on an unbleached Kraft paper weighing 72 g/m², with the aid of an air doctor blade system. The whole is then dried by passing it for 30 seconds through a tunnel-oven heated to 150° C.

The unbleached Kraft paper coated in this way with a continuous thin film of organo-silicon polymer (about 1.3 g/m²) is used as a material possessing non-stick properties towards sticky or pitchy substances (pastry, confectionery, molten tars and bitumens and the customary adhesives). The ease with which these substances detach from the treated surface of the paper is unmistakable.

By way of comparison, attempts were made to produce an aqueous emulsion containing vinyltris(methoxyethoxysilane) by passing a mixture containing 8 parts of this silane, 0.6 part of the n-decyl monoether of a polyethylene glycol with 6—$CH_2CH_2O$— units and 11.4 parts of water through a colloid mill. The emulsion obtained is only stable for some hours and thereafter breaks, with the formation of gelled products; it can thus not be used in place of the solution (M), which is stable for at least 1 year.

EXAMPLE 8

A stable and homogeneous solution comprising the following is used:

| | |
|---|---|
| dibutyl-tin diacetate | 4 parts |
| ethyl polysilicate containing 40% of silica | 10 parts |
| Emulsifier E₄ of Example 5 | 4 parts |

The solution is prepared by simply mixing the 3 components at ambient temperature. 0.6 part of this solution is added to the aqueous emulsion (G) mentioned in Example 7 and after stirring an aqueous emulsion which is stable for several days at ambient temperature is obtained. The same type of unbleached Kraft paper as described in the preceding example is treated in the same way as described in the preceding example and it is found that the paper shows marked non-stick properties towards sticky and pitchy substances.

By way of comparison, attempts were made to prepare an aqueous emulsion by replacing, amongst the components of the above solution, the 4 parts of emulsifier $E_4$ by 25 parts of water and 1.1 parts of the n-undecyl monoether of a polyethylene glycol having an average of 6 —$CH_2CH_2O$— units; the new composition is then passed through a colloid mill and it is found that the emulsion obtained is only stable for a few hours at ambient temperature and can thus not be used as a catalyst emulsion for the emulsion (G).

EXAMPLE 9

An aqueous emulsion containing the following is used: α-ω-dihydroxydimethylpolysiloxane oil of viscosity

| | | |
|---|---|---|
| 5,000 cPo at 25° C | 32 | parts |
| methylpolysiloxane resin consisting of $CH_3SiO_{1.5}$ and $(CH_3)_2SiO$ units respectively present in the numerical ratio of 71/29 | 8.4 | parts |
| polyvinyl alcohol of saponification number 105, of which the viscosity of a 4% strength aqueous solution is about 25 cPo at 25° C | 1.65 | part |
| water | 957.95 | parts |

To catalyse the above emulsion, 4 parts of the emulsion (H) described in Example 7 are used. For crosslinking the emulsion, 4 parts of a solution containing the following are used:

| | | |
|---|---|---|
| methyltriethoxysilane | 8 | parts |
| emulsifier $E_4$ of Example 5 | 2 | parts |

The 3 compositions are mixed and an aqueous solution which is stable for at least 72 hours at ambient temperature is obtained. This emulsion is deposited on the face of an unbleached polyethylene-backed Kraft paper weighing 65 g/m², at the rate of 30 g/m², by means of an airdoctor blade system. After drying by passing through a tunnel oven, heated to 150° C, for 30 seconds, the paper is found to be covered with a film-forming coating of an organo-silicon polymer (about 1.2 g/m²) which adheres firmly to the polyethylene film whilst retaining marked non-stick properties towards sticky and pitchy substances.

We claim:
1. A surface-active composition comprising, by weight:
   a. 45 to 90% of at least one n-alkyl monoether of a polyethylene glycol, containing 4 to 9 —$CH_2CH_2O$— units, the n-alkyl radicals containing 5 to 15 carbon atoms,
   b. 5 to 35% of a sodium dialkylsulphosuccinate, the linear or branched alkyl radicals containing 6 to 12 carbon atoms,
   c. 2 to 17% of at least one acid selected from oleic, linoleic, linolenic and ricinoleic acid and
   d. 1.5 to 12% of at least one amine selected from triethanolamine and N-hydroxyethylmorpholine.

2. A composition according to claim 1 wherein component (b) is sodium di(2-ethylhexyl) sulphosuccinate, sodium dihexylsulphosuccinate, sodium dinonyl sulphosuccinate or sodium dioctyl sulphosuccinate.

3. A composition according to claim 1 wherein component (c) is oleic or linoleic acid and component (d) is triethanolamine.

4. A process for preparing a composition as defined in claim 1 wherein components (a) and (b) are mixed together first and components (c) and (d) then incorporated into the mixture of components (a) and (b).

* * * * *